US012758108B2

(12) United States Patent
Elliott et al.

(10) Patent No.: US 12,758,108 B2
(45) Date of Patent: Oct. 13, 2026

(54) PERSONAL HEALTH DATA COLLECTION

(71) Applicant: LMD IP, LLC, Oklahoma City, OK (US)

(72) Inventors: Christopher Elliott, St-Sulpice (CH); Mark-Eric Jones, Penthalaz (CH); Shady Gawad, Lonay (CH); Gabriel Klein, Montpreveyres (CH); Didier Clerk, Monthey (CH); Philippe Bauser, Divonne les Baines (FR)

(73) Assignee: LMD IP, LLC, Oklahoma City, OK (US)

( * ) Notice: Subject to any disclaimer, the term of this patent is extended or adjusted under 35 U.S.C. 154(b) by 894 days.

(21) Appl. No.: 17/786,955

(22) PCT Filed: Dec. 14, 2020

(86) PCT No.: PCT/IB2020/061894
§ 371 (c)(1),
(2) Date: Jun. 17, 2022

(87) PCT Pub. No.: WO2021/124071
PCT Pub. Date: Jun. 24, 2021

(65) Prior Publication Data

US 2023/0034358 A1 Feb. 2, 2023

(30) Foreign Application Priority Data

Dec. 17, 2019 (GB) ..................................... 1918576
Dec. 17, 2019 (GB) ..................................... 1918579

(51) Int. Cl.
*A61B 5/022* (2006.01)
*A61B 5/00* (2006.01)
(Continued)

(52) U.S. Cl.
CPC ...... *A61B 5/02225* (2013.01); *A61B 5/02007* (2013.01); *A61B 5/02028* (2013.01);
(Continued)

(58) Field of Classification Search
CPC .... A61B 5/02225; A61B 5/28; A61B 5/02007
(Continued)

(56) References Cited

U.S. PATENT DOCUMENTS 4,440,716 A 4/1984 Smith
4,610,256 A 9/1986 Wallace et al.
(Continued)

FOREIGN PATENT DOCUMENTS

AU 2001259012 B2 7/2006
CN 1383371 A 12/2002
(Continued)

OTHER PUBLICATIONS

International Search Report and Written Opinion for PCT/IB2020/061894, dated Mar. 17, 2021.
(Continued)

*Primary Examiner* — Nadia A Mahmood
(74) *Attorney, Agent, or Firm* — Crowe & Dunlevy, P.C.

(57) ABSTRACT

The invention disclosed herein relates to improvements in the collection personal health data. It further relates to a Personal Health Monitor (PHM), which may be a Personal Hand Held Monitor (PHHM), that incorporates a Signal Acquisition Device (SAD) and a processor with its attendant screen and other peripherals. The SAD is adapted to acquire signals which can be used to derive one or more measurements of parameters related to the health of a user. The computing and other facilities of the PHM with which the SAD is integrated are adapted to control and analyse signals received from the SAD. The personal health data collected by the SAD may include data related to one or more of blood
(Continued)

pressure, pulse rate, blood oxygen level ($SpO_2$), body temperature, respiration rate, ECG, cardiac output, heart function timing, arterial stiffness, tissue stiffness, hydration, blood viscosity, blood pressure variability, the concentration of constituents of the blood such as glucose or alcohol and the identity of the user.

17 Claims, 4 Drawing Sheets

(51) Int. Cl.
*A61B 5/02* (2006.01)
*A61B 5/021* (2006.01)
*A61B 5/0285* (2006.01)
*A61B 5/28* (2021.01)

(52) U.S. Cl.
CPC ........ *A61B 5/02125* (2013.01); *A61B 5/0285* (2013.01); *A61B 5/28* (2021.01); *A61B 5/4875* (2013.01); *A61B 5/6843* (2013.01); *A61B 5/7278* (2013.01); *A61B 2560/0223* (2013.01)

(58) Field of Classification Search
USPC .......... 600/513
See application file for complete search history.

(56) References Cited

U.S. PATENT DOCUMENTS 4,641,973 A 2/1987 Nestler et al.
4,686,764 A 8/1987 Adams et al.
4,718,426 A 1/1988 Russell
4,785,820 A 11/1988 Brooks
4,882,492 A 11/1989 Schlager
4,920,972 A 5/1990 Frank et al.
5,007,423 A 4/1991 Branstetter et al.
5,050,612 A 9/1991 Matsumura
5,099,842 A 3/1992 Mannheimer et al.
5,099,852 A 3/1992 Meister et al.
5,137,023 A 8/1992 Mendelson et al.
5,140,990 A 8/1992 Jones et al.
5,167,230 A 12/1992 Chance
5,190,041 A 3/1993 Palti
5,299,570 A 4/1994 Hatschek
5,348,003 A 9/1994 Caro
5,361,758 A 11/1994 Hall et al.
5,424,545 A 6/1995 Block et al.
5,511,546 A 4/1996 Hon
5,581,038 A 12/1996 Lampropoulos et al.
5,638,816 A 6/1997 Kiani-Azarbayjany et al.
5,752,919 A 5/1998 Schrimpf
5,838,016 A 11/1998 Johnson
5,862,805 A 1/1999 Nitzan
5,865,755 A 2/1999 Golub
5,910,109 A 6/1999 Peters et al.
5,931,790 A 8/1999 Peel
6,064,898 A 5/2000 Aldrich
6,159,157 A 12/2000 Archibald et al.
6,172,743 B1 1/2001 Kley et al.
6,223,063 B1 4/2001 Chaiken et al.
6,241,679 B1 6/2001 Curran
6,302,844 B1 10/2001 Walker et al.
6,340,349 B1 1/2002 Archibald et al.
6,443,906 B1 9/2002 Ting et al.
6,475,153 B1 11/2002 Khair et al.
6,511,436 B1 1/2003 Asmar
6,741,876 B1 5/2004 Scecina et al.
7,020,514 B1 3/2006 Wiesel
7,396,331 B2 7/2008 Mack et al.
7,418,284 B2 8/2008 Delonzor et al.
7,641,614 B2 1/2010 Asada et al.
8,795,185 B2 8/2014 Cho
8,814,800 B2 8/2014 Fortin et al.
9,820,696 B1 11/2017 Narasimhan
10,342,438 B2 7/2019 Moon et al.
10,398,324 B2 9/2019 Mukkamala et al.
11,357,413 B2 6/2022 Little et al.
11,457,824 B2 10/2022 Yuen
2002/0035332 A1 3/2002 Chen et al.
2002/0041166 A1 4/2002 Grubisic
2002/0120288 A1 8/2002 Dedo
2002/0173709 A1 11/2002 Fine et al.
2003/0004421 A1 1/2003 Ting et al.
2003/0036685 A1 2/2003 Goodman
2004/0169190 A1 9/2004 Ueno et al.
2004/0199061 A1 10/2004 Glukhovsky
2005/0043597 A1 2/2005 Xie
2005/0137469 A1 6/2005 Berman et al.
2005/0216654 A1 9/2005 Barth et al.
2005/0234310 A1 10/2005 Alwan et al.
2005/0234312 A1 10/2005 Suzuki et al.
2005/0256412 A1 11/2005 Shimazu et al.
2006/0183983 A1 8/2006 Acosta et al.
2007/0026553 A1 2/2007 Buckley et al.
2007/0027375 A1 2/2007 Melker et al.
2007/0073170 A1 3/2007 Danehorn et al.
2007/0093701 A1 4/2007 Myers et al.
2007/0100213 A1 5/2007 Dossas et al.
2007/0100243 A1 5/2007 Lam et al.
2007/0203405 A1 8/2007 Shimomura
2007/0221848 A1 9/2007 Johnson et al.
2007/0285226 A1 12/2007 Yi
2008/0091092 A1 4/2008 Al-Ali
2008/0318563 A1 12/2008 Ross et al.
2009/0069859 A1 3/2009 Whinnett et al.
2009/0143688 A1 6/2009 Rekimoto
2009/0209834 A1 8/2009 Fine
2009/0216132 A1 8/2009 Orbach
2009/0219154 A1 9/2009 Kukula et al.
2010/0013642 A1 1/2010 Watson et al.
2010/0049059 A1 2/2010 Ha et al.
2010/0087720 A1 4/2010 Addison
2010/0106029 A1 4/2010 Fraden
2010/0160797 A1 6/2010 Banet et al.
2010/0168590 A1 7/2010 Kasama
2010/0204588 A1 8/2010 Kim et al.
2010/0249619 A1 9/2010 Kasama
2011/0054330 A1 3/2011 Pfeiffer et al.
2011/0105918 A1 5/2011 Fortin et al.
2011/0118613 A1 5/2011 Yokoyama et al.
2011/0125028 A1 5/2011 Wood et al.
2011/0125034 A1 5/2011 Tsuji et al.
2011/0166461 A1 7/2011 Suesstrunk et al.
2011/0237905 A1 9/2011 Kutzik et al.
2012/0128143 A1 5/2012 Rudman
2012/0190944 A1 7/2012 Thaveeprungsriporn et al.
2012/0234310 A1 9/2012 Wallgren
2012/0277546 A1 11/2012 Soykan et al.
2012/0330192 A1 12/2012 Casey
2013/0182144 A1 7/2013 Klinghult
2013/0237865 A1 9/2013 Sato et al.
2014/0024905 A1 1/2014 Sarrafzadeh et al.
2014/0066793 A1 3/2014 Mukkamala et al.
2014/0135592 A1 5/2014 Ohnemus et al.
2014/0142445 A1 5/2014 Banet et al.
2014/0155712 A1 6/2014 Lamego et al.
2014/0221859 A1 8/2014 Albert
2014/0257050 A1 9/2014 Kuroda et al.
2015/0031965 A1 1/2015 Visvanathan et al.
2015/0065830 A1 3/2015 Karp et al.
2015/0245775 A1 9/2015 Fonte et al.
2015/0269825 A1 9/2015 Tran
2015/0374248 A1 12/2015 Hu et al.
2016/0007865 A1 1/2016 Sakata et al.
2016/0073905 A1 3/2016 Murai et al.
2016/0081565 A1 3/2016 Kinoshita et al.
2016/0198955 A1 7/2016 Fortin
2016/0213266 A1 7/2016 Fuke et al.
2016/0213332 A1 7/2016 Ukawa et al.
2016/0262695 A1 9/2016 Zhang et al.
2016/0325143 A1 11/2016 Yuen et al.
2017/0181648 A1 6/2017 Ohno et al.

(56) References Cited

U.S. PATENT DOCUMENTS

| | | | |
|---|---|---|---|
| 2017/0181649 | A1 | 6/2017 | Carter et al. |
| 2017/0209053 | A1 | 7/2017 | Pantelopoulos et al. |
| 2017/0209055 | A1 | 7/2017 | Pantelopoulos et al. |
| 2017/0319079 | A1 | 11/2017 | Mezenok et al. |
| 2017/0340219 | A1 | 11/2017 | Sullivan et al. |
| 2017/0354331 | A1 | 12/2017 | Borkholder et al. |
| 2017/0360314 | A1 | 12/2017 | Proença et al. |
| 2018/0055375 | A1 | 3/2018 | Martinez et al. |
| 2018/0177413 | A1 | 6/2018 | Kwon et al. |
| 2018/0325398 | A1 | 11/2018 | Nitzan |
| 2021/0204824 | A1 | 7/2021 | Wang et al. |
| 2021/0293616 | A1 | 9/2021 | Capella et al. |

FOREIGN PATENT DOCUMENTS

| | | | | |
|---|---|---|---|---|
| CN | 1453565 | A | 11/2003 | |
| CN | 1568158 | A | 1/2005 | |
| CN | 101229058 | A | 7/2008 | |
| CN | 101264011 | A | 9/2008 | |
| CN | 101427923 | A | 5/2009 | |
| CN | 101484065 | A | 7/2009 | |
| CN | 101730502 | A | 6/2010 | |
| CN | 201672970 | U | 12/2010 | |
| CN | 102144917 | A | 8/2011 | |
| CN | 102481105 | A | 5/2012 | |
| CN | 202235386 | U | 5/2012 | |
| CN | 102613966 | A | 8/2012 | |
| CN | 103327894 | A | 9/2013 | |
| CN | 204121024 | U | 1/2015 | |
| CN | 105095635 | A | 11/2015 | |
| CN | 108577820 | A | 9/2018 | |
| CN | 109480802 | A | 3/2019 | |
| DE | 102004001931 | A1 | 8/2005 | |
| DE | 102005004143 | A1 | 8/2006 | |
| EP | 0041696 | A1 | 12/1981 | |
| EP | 1859734 | A1 | 11/2007 | |
| EP | 2637559 | A1 | 9/2013 | |
| EP | 3469984 | A1 | 4/2019 | |
| JP | S5752440 | A | 3/1982 | |
| JP | S61127703 | U | 8/1986 | |
| JP | H01104243 | A | 4/1989 | |
| JP | H04180729 | A | 6/1992 | |
| JP | H06311972 | A | 11/1994 | |
| JP | H07501230 | A | 2/1995 | |
| JP | H07184867 | A | 7/1995 | |
| JP | 2000506258 | A | 5/2000 | |
| JP | 2000237195 | A | 9/2000 | |
| JP | 2001190507 | A | 7/2001 | |
| JP | 2001514916 | A | 9/2001 | |
| JP | 2002027051 | A | 1/2002 | |
| JP | 2002518075 | A | 6/2002 | |
| JP | 2002224055 | A | 8/2002 | |
| JP | 2003254836 | A | 9/2003 | |
| JP | 2003290226 | A | 10/2003 | |
| JP | 2003530191 | A | 10/2003 | |
| JP | 2004344308 | A | 12/2004 | |
| JP | 2005148038 | A | 6/2005 | |
| JP | 2005190149 | A | 7/2005 | |
| JP | 2005218501 | A | 8/2005 | |
| JP | 3725256 | B2 | 9/2005 | |
| JP | 2006072665 | A | 3/2006 | |
| JP | 2006239114 | A | 9/2006 | |
| JP | 2007061186 | A | 3/2007 | |
| JP | 2007111524 | A | 5/2007 | |
| JP | 2007209374 | A | 8/2007 | |
| JP | 2007236732 | A | 9/2007 | |
| JP | 3140916 | U | 3/2008 | |
| JP | 2009006037 | A | 1/2009 | |
| JP | 2009183628 | A | 8/2009 | |
| JP | 2009233284 | A | 10/2009 | |
| JP | 2010506625 | A | 3/2010 | |
| JP | 2010220949 | A | 10/2010 | |
| JP | 2012515630 | A | 7/2012 | |
| KR | 930002822 | B1 | 4/1993 | |
| KR | 20030057536 | A | 7/2003 | |
| KR | 20080090552 | A | 10/2008 | |
| KR | 20120122305 | A | 11/2012 | |
| RU | 2005103835 | A | 8/2005 | |
| RU | 2511278 | C2 | 4/2014 | |
| WO | 9203967 | A2 | 3/1992 | |
| WO | 0156472 | A1 | 8/2001 | |
| WO | 2001065810 | A1 | 9/2001 | |
| WO | 0230277 | A2 | 4/2002 | |
| WO | 02094094 | A1 | 11/2002 | |
| WO | 2004012580 | A2 | 2/2004 | |
| WO | 2008078271 | A1 | 7/2008 | |
| WO | 2008110949 | A1 | 9/2008 | |
| WO | 2009113346 | A1 | 9/2009 | |
| WO | 2010017973 | A1 | 2/2010 | |
| WO | 2011073894 | A1 | 6/2011 | |
| WO | 2012060732 | A1 | 5/2012 | |
| WO | 2012064326 | A1 | 5/2012 | |
| WO | 2013/001265 | A2 | 1/2013 | |
| WO | 2014/125355 | A1 | 8/2014 | |
| WO | WO-2014125431 | A1 * | 8/2014 | ......... A61B 5/14532 |
| WO | 2015184029 | A1 | 12/2015 | |
| WO | 2016/096919 | A1 | 6/2016 | |
| WO | 2017/140748 | A2 | 8/2017 | |
| WO | 2017/198981 | A1 | 11/2017 | |
| WO | 2019/211807 | A1 | 11/2019 | |
| WO | 2020053290 | A1 | 3/2020 | |
| WO | 2020144397 | A1 | 7/2020 | |

OTHER PUBLICATIONS

World Health Organization, Global Status Report on Noncommunicable Diseases 2010, ISBN 978 92 4 156422 9, 164 pages.

Healthcare Unwired, Health Research Institute, New Business models delivering care anywhere, PricewaterhouseCoopers, Sep. 2010, 40 pages.

Westerhof, et al., "Cardiac muscle mechanics", in "Snapshots of hemodynamics", 2nd ed., New York: Springer, 2005, 4-192.

"Lowess Smoothing in Statistics: What is it?", http://www.statisticshowto.com/lowesssmoothing/, Accessed on Dec. 14, 2018, 5 pages.

Al-Jaafreh, et al., "New Model to estimate Mean Blood Pressure by Heart Rate with Stroke Volume changing influence", EMBS Annual International Conference, Proceedings of the 28th IEEE, Aug. 30-Sep. 3, 2006, 2006, 1803-1805.

Allen , "Photoplethysmography and its application in clinical physiological measurement", Physiological Measurement (28), 2007, R1-R39.

Azmal, et al., "Continuous Measurement of Oxygen Saturation Level Using Photoplethysmography Signal", International Conference on Biomedical and Pharmaceutical Engineering, Singapore, Dec. 11-14, 2006, 504-507.

Bank, et al., "Direct Effects of Smooth Muscle Relaxation and Contraction on In Vivo Human Brachial Artery Elastic Properties", Circulation Research; vol. 77, Nov. 1995, 1008-1016.

Chua, et al., "Freescale Semiconductor Application Note AN1571, Digital Blood Pressure Meter", 2005, 1-8.

Danael, Goodarz , et al., "National, regional, and global trends in fasting plasma glucose and diabetes prevalence since 1980: systematic analysis of health examination surveys and epidemiological studies with 370 country-years and 2.7 million participants", www.thelancet.com, Jul. 2, 2011, vol. 378, pp. 31-40.

Drzewiecki, et al., "Theory of Oscillometric Maximum and the Systolic and Diastlic Detection Ratios", Annals of Biomedical Engineering (22), 1994, 88-96.

Fine, Ilya, "Glucose Correlation with Light Scattering Patterns", from: Handbook of Optical Sensing of Glucose in Biological Fluids and Tissues CRC Press, 2009, 44 pages.

Gee, Tim , "Apple Targets Health Care with iPhone 3.0 OS, Medical Connectivity", http://medicalconnectivity.com/2009/03/19/apple-targets-health-care-with-iphone-30-os/, Mar. 19, 2009, 1-13.

Imholz , et al., "Fifteen Years Experience with Finger Arterial Pressure Monitoring: Assessment of the Technology", Cardiovascular Research, Mar. 3, 1998, 605-616.

(56) References Cited

OTHER PUBLICATIONS

Karr, C. K., et al., "Genetic algorithm applied to least squares curve fitting", (No. 9339), US Department of the Interior, Bureau of Mines, 1991.

Klonoff, "Noninvasive Blood Glucose Monitoring", Diabetes Care 20(3), Mar. 1997, 433-437, 5 pages.

Koohi, et al., "Coefficient-Free Blood Pressure Estimation Based on Arterial Lumen Area Oscillations in Oscillometric Methods", IEEE 9th Int'l Symposium on Intelligent Signal Processing, 2015, 6 pages.

Ladeira , et al., "Strategic Applications Agenda, Version 3, Working Group on Leading Edge Applications", www.emobility.eu.org, Jan. 2010, 396 pages.

Langewouters, et al., "Pressure-Diameter Relationships of Segments of Human Finger Arteries", Clinical Physics and Physiological Measurement 7(1), 1986, 43-55.

Lee, C. , et al., "Relations between ac-dc components and optical path length in photoplethysmography", Journal of biomedical optics, 16(7), 2011, 077012.

Leslie, Ian , et al., "Mobile Communications for Medical Care, Final Report", Apr. 21, 2011, 1-120.

Padilla, et al., "Cariovasc Eng., Pulse Wave Velocity and digital vol. pulse as indirect estimators of blood pressure: Pilot study on Healthy Volunteers", 2009, 9 pages.

Painter, "The velocity of the arterial pulse wave: a viscous-fluid shock wave in an elastic tube", Theo Biol Med Model 5: 15, 2008.

Papaioannou , et al., "The systolic volume balance method for the noninvasive estimation of cardiac output based on pressure wave analysis", Am. J. Physiol. Heart Circ. Physiol., 302, 2012, H2064-H2073.

Reisner, et al., "Utility of the Photoplethysmogram in Circulatory Monitoring", Anesthesology, vol. 108, No. 5, 2008, 950-958.

Shaltis, Phillip Andrew, "A Wearable Blood Pressure Sensor Using Oscillometric Photoplethysmography and Micro Accelerometers", Ph.D. thesis. Cambridge (MA): Massachusetts Institute of Technology, Dept of Mechanical Engineering, 2007, 1-124.

Silva, Jennifer MD, "Smartphone-enabled ECG devices effective at detecting arrhythmias in children", Cardiology Today, Jun. 10, 2014.

Smulyan, et al., "Blood Pressure Measurement: Retrospective and Prospective Views", American Journal of Hypertension 24(6), Jun. 2011, 628-634.

Solosenko , et al., "Automatic premature ventricular contraction detection in photoplethysmographic signals", Biomedical Circuits and Systems Conference (BioCAS), IEEE, 2014.

Stergiopolus, et al., "Physical Basis of Pressure Transfer from Periphery to Aorta; A Model-Based Study", Am. J. Physiol. 274, 1998, HI386-HI392.

Tanaka, G. , et al., "A novel photoplethysmography technique to derive normalized arterial stiffness as a blood pressure independent measure in the finger vascular bed", Physiological Measurement, 32(11), 2011, 1869.

Teng , et al., "Proceedings of the 25th Annual International Conference of the IEEE EMBS, Cancun, Mexico", Sep. 17-21, 2003, 4 pages (3153-3156).

Timm, U , et al., "LED Based Sensor System for Non-Invasive Measurement of the Hemoglobin Concentration in Human Blood", IFMBE Proceedings 2008, vol. 23, 2008, 825-828.

Vardoulis , et al., "On the estimation of total arterial compliance form aortic pulse wave velocity", Ann. Biomed. Eng., 40, 2012, 2619-2626.

"Why Blood Viscosity Testing Could Be an Important Key for Covid-19- Treatment," Journal of Invasive Cardiology, retrieved at https://www.printfriendly.com/p/g/86prGZ, Aug. 3, 2020, 5 Pages.

Gircys et al., "Photoplethysmography-Based Continuous Systolic Blood Pressure Estimation Method for Low Processing Power Wearable Devices", Appl. Sci., 2019, vol. 9, No. 11, 2236, 16 Pages.

Liu et al., "Using the Characteristics of Pulse Waveform to Enhance the Accuracy of Blood Pressure Measurement by a Multi-Dimension Regression Model", Applied Sciences, vol. 9, No. 14, Jul. 2, 2019, 11 pages.

Tavallai et al., "Artificial Intelligence Estimation of Carotid-Femoral Pulse Wave Velocity using Carotid Waveform", Scientific Reports 8, Article No. 1014, 2018, 12 Pages.

"International Search Report" for PCT/IB2020/061894, dated Jun. 24, 2021.

Examination Report in European Patent Application No. 20828128.7 dated Jun. 18, 2025.

First Office Action for Chinese Patent Application No. 202080096718.9, dated Feb. 27, 2025.

Second Office Action for Chinese Application No. 202080096718.9 dated Sep. 29, 2025.

Arquivos Brasileiros de Cardiologia Journal, Sociedade Brasileira de Cardiologia MCMXLIII; vol. 85, Suppl. 2, Jul. 2005, 25 pages.

Healthcare unwired, Health Research Institute, New business models delivering care anywhere, PricewaterhouseCoopers, Sep. 2010, 40 days.

""Coefficient-free blood pressure estimation based on arterial lumen area oscillations in oscillometric methods"", 2015 IEEE 9th International Symposium on Intelligent Signal Processing (WISP) Proceedings, IEEE, May 15, 2015 (May 15, 2015), pp. 1-6, XP033168029, DOI: 10.1109/WISP.2015.7139181.

Azmal , et al., "Intl. Conf. Biomedical and Pharmaceutical Engineering 2006", (ICBPE 2006), 2006, 504-507.

Jaafreh , et al., "New Model to estimate Mean Blood Pressure by Heart Rate with Stroke Volume changing influence", Proceedings of the 28th International Conference of the IEEE EMBS Annual International Conference, New York, NY, Aug. 30-Sep. 3, 2006, 1803-1805.

Notification to Go through Formalities of Registration, dated Jul. 1, 2026, Chinese Application No. 2020800967189.

* cited by examiner

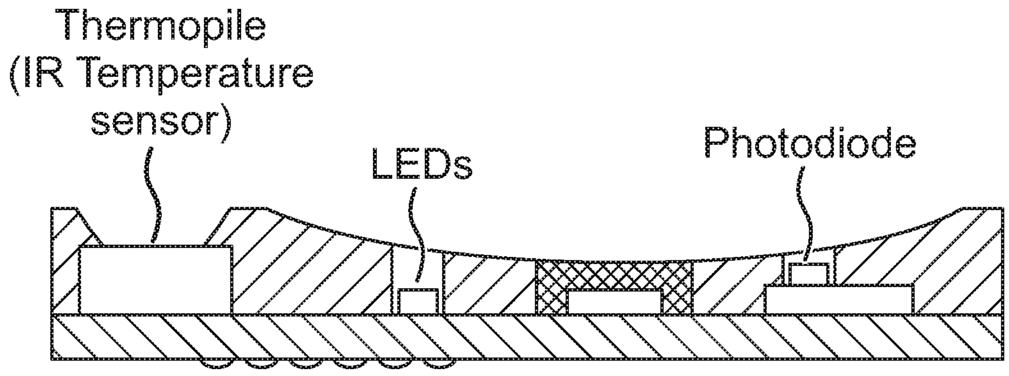
FIG. 5
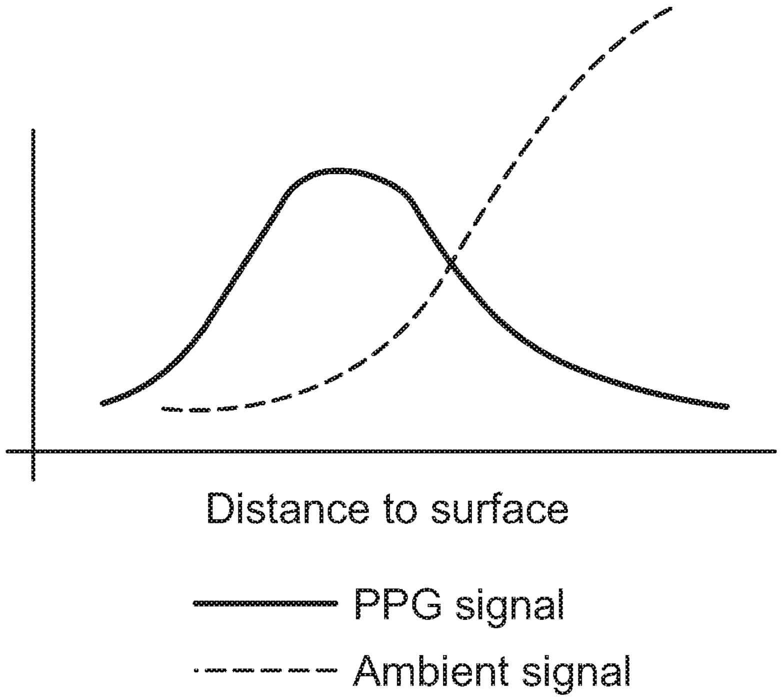

PERSONAL HEALTH DATA COLLECTION

CROSS-REFERENCE TO RELATED APPLICATIONS

This application is the National Stage of International Patent Application No. PCT/IB2020/061894, filed Dec. 14, 2020, which claims priority to Great Britain Patent Application No. 1918576.8, filed Dec. 17, 2019 and Great Britain Application No. 1918579.2, filed Dec. 17, 2019, the disclosures of which are incorporated herein by reference in their entireties for any and all purposes.

FIELD OF THE INVENTION

The invention disclosed herein relates to improvements in the collection of personal health data. It further relates to a Personal Health Monitor (PHM), which may be a Personal Hand Held Monitor (PHHM), which incorporates a Signal Acquisition Device (SAD) and a processor with its attendant screen and other peripherals. The SAD is adapted to acquire signals which can be used to derive one or more measurements of parameters related to the health of a user. The computing and other facilities of the PHM with which the SAD is connected or integrated are adapted to control and analyse signals received from the SAD. The personal health data collected by the SAD may include data related to one or more of blood pressure, pulse rate, blood oxygen level ($SpO_2$), body temperature, respiration rate, ECG, cardiac output, heart function timing, arterial stiffness, tissue stiffness, hydration, the concentration of constituents of the blood such as glucose or alcohol, blood viscosity, blood pressure variability and the identity of the user.

GENERAL BACKGROUND

Many methods for measuring blood pressure are known, such as the oscillometric method (using measurements of pressure in a cuff), the PPG optical method (using a measurement of the absorption of light by blood in an artery), the auscultation method (using change in sound as blood flows through an artery) or a direct method (using ultrasound imaging or any other way of detecting the difference in luminal area or size of the artery as it changes from occluded to patent)

WO2013/001265 (PCT1) discloses a Personal Hand-Held Monitor (PHHM) in which a signal acquisition device (SAD) is integrated with a Personal Hand Held Computing Device (PHHCD), such as a cell phone, and is adapted for the measurement of, for example, blood pressure or one or more of several other health-related parameters. The SAD is adapted to be pressed against a body part or to have a body part pressed against it, for example, where the body part is the side of a finger. This permits a cuff-less occlusion measurement. The SAD also includes an electrical sensor which can be used to detect a 1-lead ECG between the two hands.

WO2014/125431 (PCT2) discloses several improvements of the invention described in PCT1, including the use of: a gel to measure pressure; a saddle-shape surface to interact with a body part; corrections for the actual position of an artery relative to the device; and the use of interactive instructions to the user.

WO/2014/125355 (PCT3) discloses improvements of the non-invasive blood analysis disclosed in PCT1 including improvements to the specificity and accuracy of the measurements.

WO2016/096919 (PCT4) discloses several further improvements of the inventions described in PCT1 and PCT2, including improvements to the gel and pressure sensing means, the use of mathematical procedures for extracting blood pressures and other signal processing inventions, a means for identifying the user, improvements to the electrical systems for measurement and several aspects of test and calibration of the device. PCT 4, page 11, lines 5 to 8 discloses that, in order to carry out a PWA, it is possible to use a camera to detect the arrival of the pulse by means of the change of colour of the skin. This allows, for example, the difference in pulse time at the face and finger to be found.

WO2017/140748 (PCT5) discloses further improvements to extracting blood pressure and several other health-related parameters that can be derived from the measured data.

WO2017/198981 (PCT6) discloses improvements to the inventions disclosed in PCT3 whereby the device can be built using small and inexpensive components.

WO2019/211807 (PCT7) discloses several improvements to the inventions disclosed above, including aspects where the device is adapted to use the fingertip or an artery in the cheek, both of which result in increased variation in applied pressure when compared to the earlier applications.

PCT1 to PCT7 are all in the name of Leman Micro Devices SA and are therefore collectively referred to as "the Leman applications". The Leman applications are hereby incorporated into the present application in their entirety by reference.

The inventions disclosed by the Leman applications are effective, reasonably accurate and easy to use, and may be integrated into a cell phone. Cell phones are manufactured in quantities of hundreds of millions and the price of their components is critical. These inventions allow the cost of blood pressure measurement to be reduced to a level that is acceptable for a cell phone, in part because they eliminate the expensive and heavy components of conventional devices that ensure a constant applied pressure.

The area of an artery changes between the times of diastole and systole because there is a change of the difference between pressure of the blood inside the artery and the pressure in the tissue surrounding the artery. This causes the artery wall to stretch. If this stretching can be detected and measured, it is possible to find the diastolic and systolic pressures without using a cuff.

This measurement principle of cuff-less occlusion thus has many advantages to the user and to global health but it requires the user actively to press the device against a body part or the body part against the device in a controlled manner. The present invention reduces the disadvantages of this by allowing much shorter measurement times and by compensating for the fluctuations of pressure that arise from the action of pressing. It also discloses additional measurement capabilities using the same collection of sensing devices.

The present invention concerns several improvements to the measurements by creating novel features for the inventions described in the Leman applications.

BACKGROUND TO THE FIRST ASPECT

There are three major classes of device for automatic non-invasive measurement of blood pressure: occlusion devices; pulse wave velocity (PWV) devices; and pulse wave analysis (PWA) devices.

Occlusion devices find the pressure that must be applied outside an artery to balance the pressure of the blood inside the artery. These give an absolute measurement of blood pressure that requires no personal calibration. Oscillometric automatic cuff devices use this occlusion principle. The Leman applications disclose a unique cuff-less occlusion device which is exploited in the first aspect of the current invention.

Pulse wave velocity (PWV) devices measure a property related to the rate at which the pressure wave propagates along the artery which, in turn, is related to the stiffness of the artery and the difference between the pressure of the blood inside the artery and the tissue outside the artery. These give a relative measure of blood pressure and so can be used to detect the change in blood pressure after they have been calibrated for the user. PWV devices are well-known and work by estimating the speed at which the pressure wave propagates along the artery by dividing the distance between two points in the arterial system by the time taken for the pulse to travel between the two points (the Pulse Transit Time PTT). There are two ways of doing this:

(i) measure the time for the pulse to travel from the heart to a remote point by using an electrical sensor to detect an electrical signal which indicates the start of the beat of the heart and using an optical sensor to detect the arrival of the pressure pulse at the remote point; the time interval between the electrical signal and the arrival of the pulse includes the delay between the electrical signal and the contraction of the heart, known as the Pre-Ejection Period (PEP); and (ii) use two or more optical sensors to detect the arrival of the pulse at different points and measure the PTT between them.

Pulse Wave Analysis (PWA) devices analyse the shape of the pulse wave measured at a remote point. This is usually measured by an optical sensor but may be measured using an ultrasound sensor, a sensor which detects displacement or a pressure sensor. The PWA is related to the pulse wave velocity. PWA devices analyse the waveform of a signal related to the area of the artery to infer blood pressure. They may do this by estimating the PWV explicitly (see, for example, Tavallali et al., Scientific Reports 8, Article number: 1014, 2018) or by direct analysis in which the contribution of velocity is implicit (see, for example, Gircys et al., Appl. Sci., 2019, 9, 2236; doi:10.3390/app9112236). PWA devices can be used to detect a change in blood pressure after they have been calibrated for the user.

A further feature of PWA and PWV devices is that they may be adapted to make an instantaneous estimate of the blood pressure on each heartbeat. This is useful both to provide biofeedback to the user and to allow the user to derive an estimate of short term blood pressure variability.

A first aspect of the present invention relates to novel ways of combining the strengths of occlusion devices, pulse wave velocity (PWV) devices and pulse wave analysis (PWA) devices to create a device that is more accurate and/or easier and quicker to use and/or offers additional measurement capabilities.

FIRST ASPECT OF THE PRESENT INVENTION

The Leman applications disclose devices that are capable of making occlusion, PWV and PWA measurements. The Leman applications disclose that two or more measurements may be combined to achieve greater accuracy. The table on page 16 of PCT1 states that:

"The combination might not just be a simple average; the processing may seek to find the most likely value in the light of all available information, using a technique such as a Bayesian estimator to take account of all data including variations between pulses."

The first aspect of the present invention goes beyond combining two values found independently and uses cooperation to make a measurement of blood pressure or another health-related parameter that is more accurate or that is easier to conduct or that is made more quickly than could be made by according to the disclosure in PCT1.

According to this aspect of the present invention, it has been discovered that it is possible to use occlusion devices, PWV devices and PWA devices in various combinations to reduce errors in the measurements of blood pressure and other health-related parameters that may result from their use and to make it easier and quicker to obtain such measurements.

Various kits and devices of the first aspect of the present invention are disclosed in independent claims 1, 2, 4, 5, 7, 8, 10 and 11 set forth in International Patent Application No. PCT/IB2020/061894 (published as WO2021/124071A1).

Preferred kits and devices of this aspect of the invention are set out in dependent claims 3, 6, 9 and 12 to 27 set forth set forth in International Patent Application No. PCT/IB2020/061894 (published as WO2021/124071A1).

In respect of the claims to a kit comprising two devices and an analysing means, the analysing means may be an entirely separate item, present entirely as part of one, the other or both of the devices or present partly as part of one or both of the devices and partly in a separate item.

In any kit of the first aspect of the invention, the analysing means may receive signals from the other components in the kit or integrated device by any suitable means, such as via cables, Wifi, Bluetooth or any other suitable means, as will be well known to the person skilled in the art.

In particular, it has been found that devices of the type disclosed in the Leman applications can be adapted to take the necessary measurements for occlusion, PWV and PWA measurement and combine two or more of the measurements cooperatively to improve the accuracy of the measurement or to improve the speed of processing in the devices disclosed in the Leman applications.

It is preferred that the part of the body which contacts the contacting means is a finger, more preferably the end of a finger, but any part of the body with an accessible artery (e.g. face, neck, toe, wrist etc) may be used. Similarly, PWV and PWA measurements may be made between any two separated parts of the body, such as measuring the start time at the heart using an electrical sensor and the finish time at a finger using an optical sensor or measuring the start time at the face using a camera viewing the face and the finish time at a finger using an optical sensor.

Preferably, the contacting means does not include a cuff.

Preferably, the kit or device is adapted to provide instructions to the user to press harder or softer create a range of applied pressure.

The change in area of the artery may be found using an optical sensor to measure the absorption of light by the blood in the artery, in a manner analogous to a pulse oximeter.

BACKGROUND TO THE SECOND ASPECT

In the devices disclosed by the Leman applications, the pressure that is used to occlude the artery is created by the muscular action of the user. Such action inevitably has fluctuations. Fluctuations between heart beats are not critical, because the algorithms of the LMD devices are able to accept data in any order, but fluctuations within a heartbeat can cause significant errors.

Conventional blood pressure measurement devices assume that the pressure in the tissue surrounding the artery is constant for the duration of a heartbeat, or at least for the period between diastole and systole. They also assume that the pressure in the tissue surrounding the artery is the same as the applied pressure. It is then simple to estimate blood pressure by plotting the value of the property related to the change in area of an artery against the applied pressure. Various proprietary algorithms are used to find diastolic and systolic blood pressures from this curve.

This approach is less effective, and therefore the measured blood pressures is less accurate, if the assumption that the pressure in the tissue surrounding the artery is constant is not valid. This may be because the change of arterial area during a heartbeat causes a significant change in the pressure in the tissue surrounding the artery. This will occur with any device but, in practice, is negligible for a device such as a conventional brachial cuff. However, it becomes more significant if the artery represents a significant fraction of the volume of the tissue being measured, such as if the body part being used for the measurement is the side of a finger. It may also occur if the mechanism for applying pressure to the tissue surrounding the artery does not apply a constant pressure, for example if it is effected by a person pressing the device against the body part or pressing the body part against the device; the person's muscles may shake with a time constant short compared to a heartbeat.

This limitation restricts the use of ways of measuring blood pressure that may be less expensive, more accurate, easier to use or smaller than the known devices, such as those ways disclosed in the Leman applications. In these, the pressure that is used to occlude the artery is created by the muscular action of the user. Such action inevitably has fluctuations. Fluctuations between heart beats are not critical, because the algorithms in the devices disclosed in the Leman applications are able to accept data in any order, but fluctuations within a heartbeat can cause significant errors.

The second aspect of the present invention overcomes or greatly mitigates the limitation due to changing pressure and so brings benefits to a range of ways of measuring blood pressure, such as those disclosed in the Leman applications.

SECOND ASPECT OF THE PRESENT INVENTION

A second aspect of the invention relates to a way of reducing the errors due to variations of the pressure between the device and the body part using isobaric analysis.

The second aspect of the present invention relates to a device for measuring blood pressure which measures a property related to the change in area of an artery as a function of the pressure applied to that artery and which can accommodate a change in applied pressure during the course of a single heartbeat.

The property related to the change in area may be the change in measured cuff pressure (the oscillometric method), the change in absorption of light (the optical method), a change in sound (the auscultation method) or the change in the luminal area or size of an artery as it changes from occluded to patent (a direct method).

Therefore, the second aspect of the present invention provides a device for the non-invasive measurement of blood pressure comprising a means for measuring the change in luminal arterial area during a heartbeat, a means for applying pressure to the body part containing the artery and a means for measuring the instantaneous pressure applied to the body part containing the artery, wherein:

the blood pressure is found by analysing the change in arterial area as a function of the instantaneous pressure applied to the body part containing the artery; and the device is adapted to make an accurate measurement of blood pressure by compensating for any significant change of the instantaneous pressure applied to the body part containing the artery during a heartbeat.

Preferably, the means for measuring the change in luminal arterial area during a heartbeat is oscillometric.

Alternatively, the means for measuring the change in luminal arterial area during a heartbeat is optical.

Further alternatively, the means for measuring the change in luminal arterial area during a heartbeat is auscultation.

Yet further alternatively, the means for measuring the change in luminal arterial area during a heartbeat is ultrasound.

Preferably, the means for compensating for the change of the instantaneous pressure applied to the body part containing the artery during a heartbeat uses a separate analysis of the values found by the means for measuring the change in luminal arterial area during a heartbeat at diastole and at systole.

Preferably, the separate analysis uses a curve-fitting algorithm to create two parametric curves, representative of the values at diastole and at systole. The curve fitting algorithm may be a Loess algorithm.

Preferably, the difference between the two parametric curves is used to create a set of pseudo heartbeats that have the same instantaneous pressure applied to the body part containing the artery at diastole and systole and wherein the set of pseudo heartbeats may then be analysed in the same way as true beats would be analysed if the instantaneous pressure applied to the body part containing the artery were not to change significantly during a heartbeat.

Preferably, the blood pressure is found by analysing the changes in arterial area as a function of the instantaneous pressure applied to the body part containing the artery.

The first and second aspects of the present invention can act synergistically in that the improvement in accuracy of the second aspect allows greater reliance on the occlusion measurement for the first aspect. It is also apparent that, although the two aspects were invented in the context of the Leman applications, their utility extends more widely to other forms of blood pressure measurement device.

BACKGROUND OF THE THIRD ASPECT

The devices disclosed by the Leman applications have several sensors that create a rich set of data. The sensors may be used cooperatively to improve the accuracy, ease of use or functionality of the device.

A third aspect of the invention uses features of the data that is or may be collected by the devices disclosed by the Leman applications to improve or extend the scope of the personal health data that is collected.

Two specific opportunities are:

to use the dynamics of the PPG data to determine the viscosity of the blood; this is increasingly recognised as a valuable diagnostic vital sign (see for example "Why Blood Viscosity Testing Could Be an Important Key for Covid-19 Treatment", Journal of Invasive Cardiology, Aug. 3, 2020); and to use the PPG signal to detect the approach of the device to a body part; the temperature measurement by detecting thermal radiation from the body part can be more accurate if the distance between the sensor and the body part is known.

THIRD ASPECT OF THE PRESENT INVENTION

PPG signals are strongly influenced by both the changes in luminal area of the artery during the heartbeat and the absorption of light by the tissue surrounding the artery, including the blood in the local blood vessels (micro-arteries and veins). When the pressure between the body part and the SAD changes, the tissue deforms and the blood flows in or out of the local blood vessels. The time constant for this deformation and blood flow is typically a few seconds.

The value of this time constant is dependent in part on the viscosity of the blood. The magnitude of the change of the PPG signal depends on the shape and constitution of the region of the body part that is illuminated and on the wavelength of the PPG light. The wavelength determines the relative absorption due to oxygenated blood, deoxygenated blood and tissue.

The third aspect of the present invention exploits both the high frequency PPG signal, resulting from the fluctuations due to variations of the luminal area of the arteries, and the low frequency PPG signal, obtained by filtering the high frequency signal. It also exploits the ability of the LMD devices to instruct the user to create a controlled applied pressure between the device and the body part and to vary that pressure on demand.

The relationship between the high and low frequency signals obtained by controlled applied pressures and the viscosity of the blood must be determined empirically. This may be done using supervised machine learning, whereby the training data set comprises:

- high and low frequency signals that are measured during various patterns of controlled applied pressure; and
- blood viscosity measured with a conventional invasive device, such as a Benson Viscometer.

The PPG optical system may also be used as a proximity detector. In devices according to the Leman applications, the LEDs that emit the light and the photodetector that detects the light are in general approximately 6 mm apart. If a reflecting or diffusive surface is moved towards the device when the LED is on, the received signal will peak at around that distance. At the same time, the ambient signal due to background light will fall as the device approaches the surface due to shadowing.

Features of the third aspect of the present invention are disclosed in independent claims 38 and 50 and preferred features of this aspect are disclosed in dependent claims 39 to 49 and 51 to 54, respectively, with reference to International Patent Application No. PCT/IB2020/061894 (published as WO2021/124071A1).

EXAMPLES

Set out below, by way of example only, are examples of the aspects of the present invention. It will be understood that the present invention is not limited to these examples. The scope of the invention is set forth in the claims below.

In the examples, reference is made to the accompanying drawings, which are provided by way of illustration only and which do not limit the scope of the invention, in which:

FIG. 5 shows a cross-section of a device according to the third aspect of the present invention together with a representation of proximity signals.

Example 1

Calibration of PWV and PWA

Figure 1:
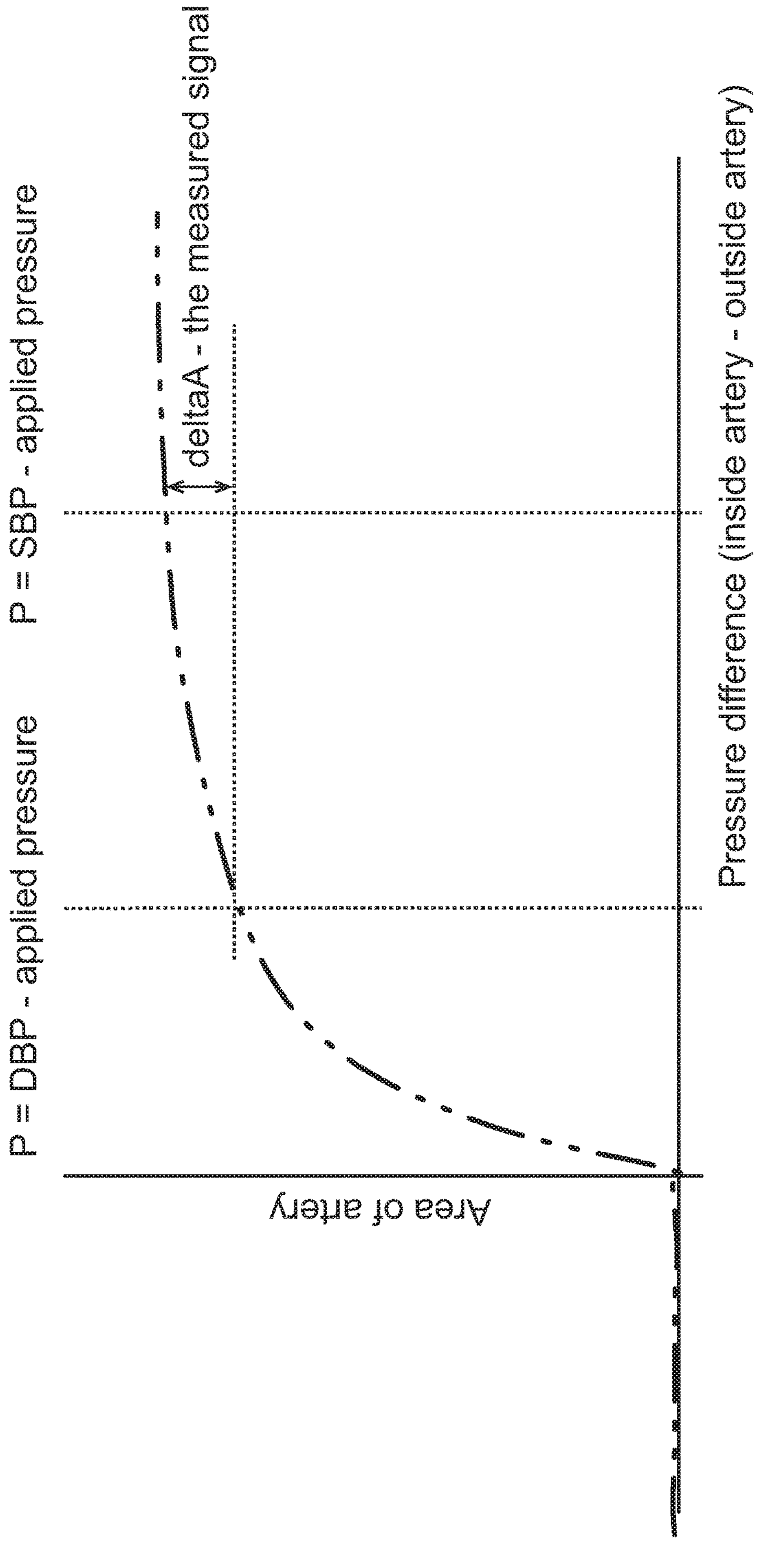
FIG. 1 is a representation of the pressure in an artery through a heartbeat and the area of that artery.

A limitation of all PWV and PWA techniques is that they must be calibrated for each user. This requires the user to make several measurements of blood pressure using an occlusion (cuff) device at the same time as measurements of PWV or PWA. These allow the PWV or PWA to be calibrated and then used to detect changes in blood pressure from that measured with the cuff. The calibration typically remains valid for a period of time of days to weeks, after which it must be repeated. This limits the utility of the PWV or PWA technique since it also needs access to a cuff device.

The absolute measurement of blood pressure by cuff-less occlusion, using a separate device as part of a kit or as part of an integrated device, may be used as a calibration for the PWV or PWA measurement. The PWV or PWA measurement may then be used to make quick and easy measurements of blood pressure until it is necessary to recalibrate.

The calibration procedure may be further enhanced by making several calibrations under different conditions, such as for example at different times of day or before and after taking exercise. Such distributed calibrations may be exploited to improve the accuracy of the subsequent PWV or PWA measurements or to extend the period until it is necessary to recalibrate.

Example 2

Stability of Pulse Wave Analysis

PWA is simple and easy to use but it is not easy to achieve adequate accuracy. One of the reasons is that the measured optical waveform depends on how hard the user presses the measurement device against the body part. The pressure sensor in the pressure means can be used with its optical sensor to generate PWA waveforms at a specific pressure by providing feedback to the user to press harder or softer. This can be used to ensure that the measurement pressure is the same as that used for calibration or can be used to provide the PWA analysis with a set of waveforms captured at different pressures.

Alternatively, the actual measured applied pressure may be used, without providing feedback to the user, as an input to the PWA algorithms so as to improve their accuracy and/or extend the time before needing re-calibration.

Example 3

Estimation of Pre-Ejection Period (PEP)

The PTT found using an electrical signal includes the PEP and so the estimated PWV will not be correct. PEP is fairly stable for an individual and so an occasional measurement of this can be used to correct the measured PTT.

PCT 4, FIG. 9 and the Ninth aspect of PCT 4 show that devices according to the Leman applications can measure PEP directly. This measurement maybe used to improve the accuracy of the PWV estimate.

Example 4

Direct Estimates of Arterial Stiffness

PWV is related to blood pressure via the arterial stiffness. If this stiffness is known, it is possible to make a more accurate estimate of that relationship and hence a more accurate estimate of blood pressure derived from PWV. Since the waveform analysed by PWA also depends on PWV, the stiffness can also be used to improve the accuracy of PWA.

PCT 4, page 11, lines 9 to 14 discloses that the local arterial stiffness can be measured directly by the Leman devices.

Example 5

Direct Estimates of Stiffness of Surrounding Tissue

The effective stiffness of an artery also depends on the stiffness of tissue surrounding it. Aspect 5 of PCT 5 discloses that devices according to the Leman applications can make an estimate of the stiffness of that tissue, including its change due to hydration. This can also be used to improve the accuracy of PWV and PWA measurements, in a similar way to the fourth example above.

Example 6

Improving the Cuff-Less Occlusion Technique using PWV Data

PCT 2, lines 24 to 30 discloses that an estimate of the arterial stiffness may be used by the cuff-less occlusion device to improve some of the techniques for extracting blood pressure from the occlusion data. It assumes that the estimate is found directly from the measured data but there is advantage in using an independent estimate, derived from a PWV or PWA measurement. This can contribute to both the accuracy of the result and the speed of processing.

The LMD applications disclose several techniques for extracting blood pressure from the data derived from the sensors that use a search or optimisation algorithm. These operate by searching the solution space, including searching for the diastolic and systolic blood pressures. An estimate of these values that is derived from PWV or PWA can be used to narrow the search space or at least to indicate starting values for the search. This reduces the time taken for the search and reduces the risk that the search selects a sub-optimum value of the solution.

Example 7

Isobaric Correction

Referring to FIG. 1, the dashed line shows the typical luminal area of an artery as a function of the difference between the instantaneous pressure of the arterial blood and the instantaneous pressure of the tissue surrounding the artery. The vertical dotted lines show the pressure difference at the time of systole (when the arterial pressure is maximum so the difference is minimum) and diastole (when the arterial pressure is minimum so the difference is maximum). The double-ended arrow, labelled deltaA, shows the change in area between systole and diastole.

Note that the exact form and vertical scale of FIG. 1 will depend on the size and stiffness of the artery, the stiffness of the surrounding tissue and the properties of the measurement means.

Figure 2:
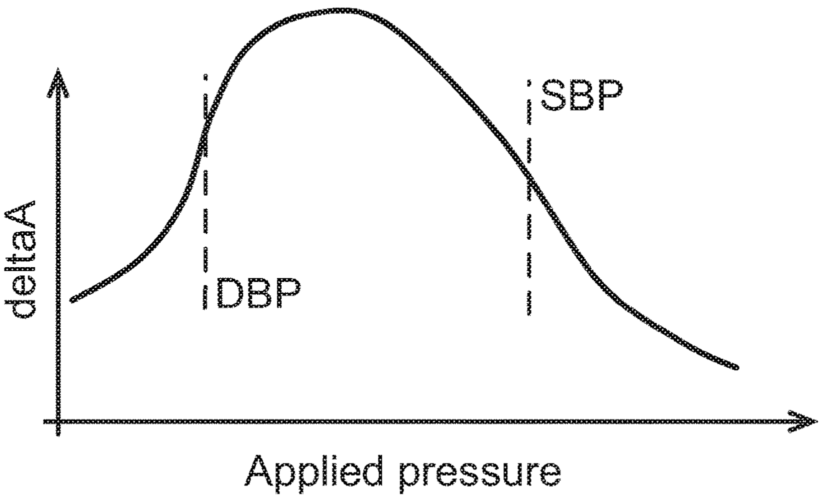
FIG. 2 illustrates how the change in area varies as a function of the applied pressure.

It is clear that the value of deltaA depends on the pressure of the tissue surrounding the artery. FIG. 2 is a typical plot of deltaA as a function of the pressure of the tissue surrounding the artery, labelled as the "applied pressure". Typical values of diastolic pressure (DBP) and systolic pressure (SBP) are marked on FIG. 2.

By plotting deltaA in FIG. 2 and, if necessary, normalising it by the maximum of deltaA in this plot, the vertical scale of FIG. 1 no longer is significant.

Figure 3:
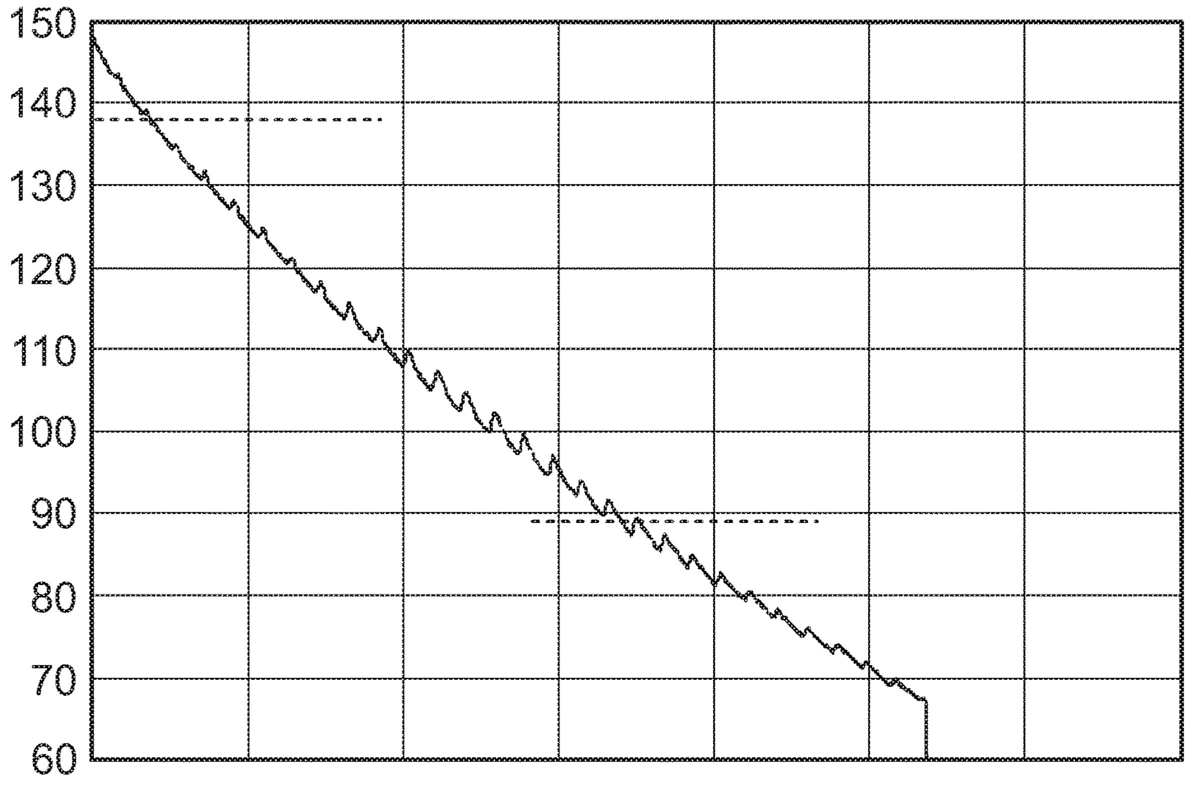
FIG. 3 is a recording of the pressure in an automatic oscillometric cuff.

This is a mature technique for use in devices that measure blood pressure where the pressure in the surrounding tissue does not change significantly within one beat. FIG. 3 illustrates this. It is a recording of the pressure in the cuff of a conventional automated oscillometric blood pressure monitor. The changes in pressure on each heartbeat are at most 2.5 mmHg, a clinically acceptable level of uncertainty. However, if these changes were much greater, either randomly or systematically, it would not be possible to make a sensible estimate of the pressure of the tissue surrounding the artery. The pressure at the time of systole would be wrong for diastole, the pressure at the time of diastole would be wrong for systole and the average pressure, as well as being wrong for both, is meaningless because FIG. 1 is non-linear.

This aspect of the present invention does not use deltaA directly. Instead, it uses the following sequence of steps:

1. Extract from the data an estimate of Anp, the luminal area of the artery at diastole on each heartbeat, and simultaneously measure the instantaneous applied pressure (assumed to be the same as the pressure surrounding the artery);
2. Plot $A_{DBP}$ as a function of the instantaneous applied pressure;
3. Fit a smoothed curve through the points representing $A_{DBP}$ versus instantaneous applied pressure to give a parametric model of $A_{DBP}$ versus instantaneous applied pressure;
4. Repeat steps 1 to 3 for $A_{SBP}$ vs instantaneous applied pressure; and
5. Create a set of "pseudo heartbeats" wherein deltaA is estimated by subtracting the value of $A_{SBP}$ given by its parametric model from the value of $A_{DBP}$ given by its parametric model, both values taken at the same instantaneous applied pressure (the term "isobaric" reflects this same instantaneous pressure).

This set of pseudo heartbeats may then be analysed using any of the analytical methods that would otherwise be used for actual heartbeats, but with a known instantaneous applied pressure.

The smoothed curve may be found using curve-fitting techniques that are well-known by persons skilled in the art, such as the Loess algorithm. As well as providing a parametric model, the parameters of the curve-fitting technique may be selected to smooth the data and so reduce the effect of measurement noise.

If the instantaneous pressure of the tissue surrounding the artery lies between the diastolic blood pressure and the systolic blood pressure, the luminal area of the artery will increase rapidly as the instantaneous arterial pressure exceeds the instantaneous pressure of the tissue surrounding the artery. It will also fall rapidly as the instantaneous arterial pressure falls below the instantaneous pressure of the tissue surrounding the artery. The timing of these two events during the heartbeat may also be used to estimate the diastolic and systolic blood pressure, in a manner analogous to the use of deltaA. For example, in an ideal model with no noise, the interval between those two times is zero if the instantaneous pressure of the tissue surrounding the artery equals or exceeds the systolic blood pressure. Similarly, that interval equals the duration of the heartbeat $T_H$ if the instantaneous pressure of the tissue surrounding the artery equals or is less than the diastolic blood pressure.

Some techniques for finding diastolic and systolic blood pressure exploit that interval. They can be compensated for the effect of varying applied pressure by the same technique as is used for deltaA, where the equivalent steps are:

1. Extract from the data an estimate of $T_R$, the time at which the luminal area of the artery grows rapidly on each heartbeat, and simultaneously measure the instantaneous applied pressure (assumed to be the same as the pressure surrounding the artery);
2. Plot $T_R$ as a function of the instantaneous applied pressure;
3. Fit a smoothed curve through the points representing $T_R$ versus instantaneous applied pressure to give a parametric model of $T_R$ versus instantaneous applied pressure;
4. Repeat steps 1 to 3 for $T_F$, the time at which the luminal area of the artery falls rapidly on each heartbeat, vs instantaneous applied pressure; and
5. Create a set of "pseudo heartbeats" wherein deltaT is estimated by subtracting the value of TR given by its parametric model from the value of $T_F$ given by its parametric model, both values being taken at the same instantaneous applied pressure.

This set of pseudo heartbeats may then be analysed using any of the analytical methods that would otherwise be used for actual heartbeats, but with a known instantaneous applied pressure. It will be apparent to a person skilled in the art that other combinations of $T_F$, $T_R$ and $T_H$ may be used, such as $(T_F-T_R)/T_H$.

Example 8

Viscosity of Blood

Figure 4:
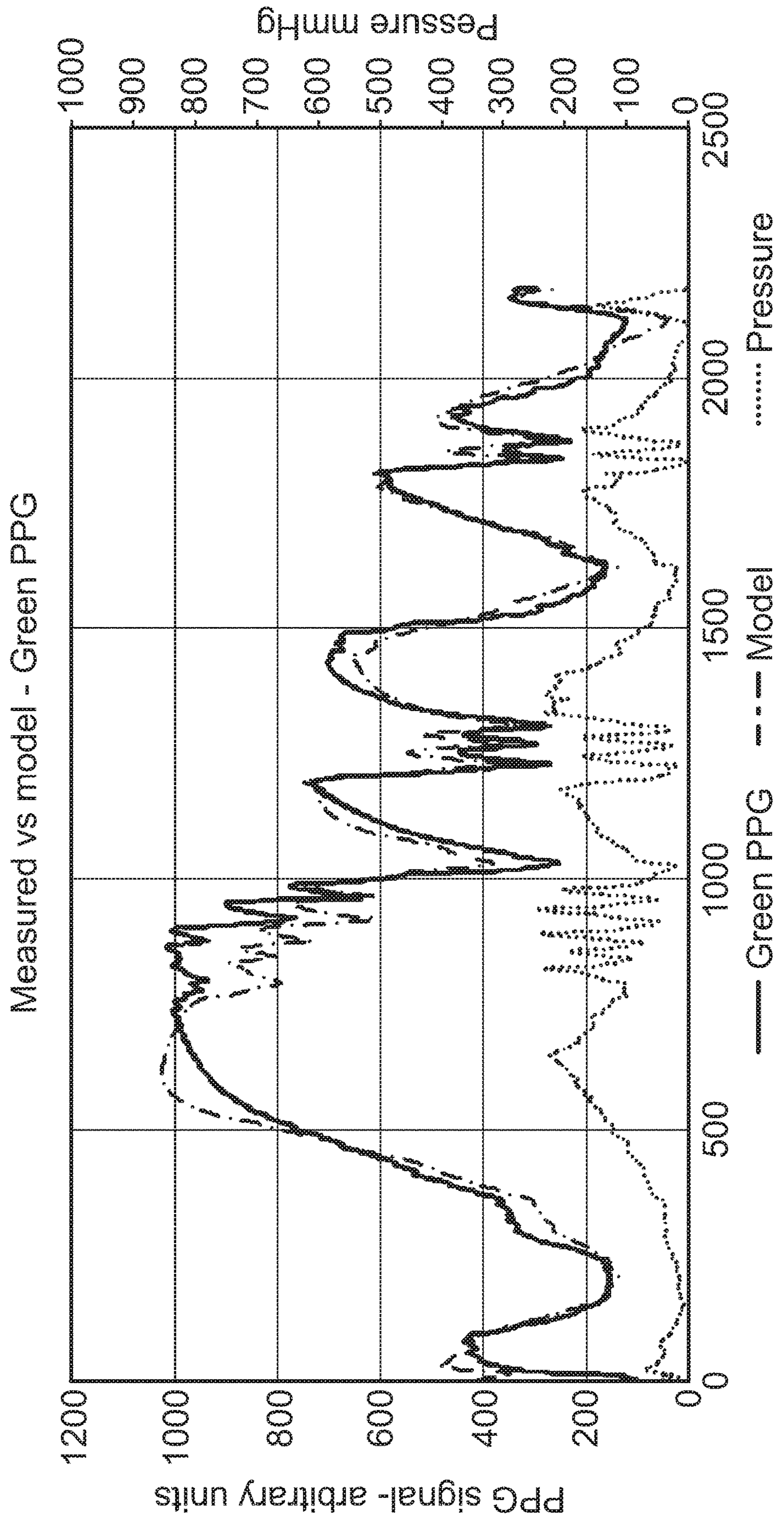
FIG. 4 illustrates the first step of an exemplary process using a measured PPG signal.

FIG. 4 illustrates the first step of an exemplary process using a measured PPG signal, as a function of pressure, in this case for green light. It shows only the low frequency signal. The high frequency fluctuations due to the arterial luminal area are too small to see on this plot.

FIG. 4 also shows how the signal can be effectively modelled using as input the pressure signal by including in the model:

a term related to the integral of pressure;

a term related to the Systolic blood pressure, above which the arteries are occluded;

a linear variation in sensitivity due to deformation of the tissue; and small terms related to the instantaneous pressure and rate of change of pressure.

Similar results may be obtained for other colours of PPG light, including but not restricted to red and infra-red, and also for the high frequency PPG signals.

The model parameters are used as inputs to the machine learning to find the combination of parameters that best predicts the viscosity of the blood.

Example 9

Proximity Detection

FIG. 5 shows a cross-section on an LMD device, together with a representation of the proximity signals. These signals may be analysed by the signal processing means to estimate the distance from the surface. That distance may be used to provide feedback to the user to place the device at the correct distance. Alternatively, the estimated distance may be used to correct errors caused by distance to any measurement that is made when not touching the body part.

It should be clearly understood that, for all of the aspects of the present invention, the examples and figures and the description thereof are provided purely by way of illustration and that the scope of the invention is not limited to this description of specific embodiments; the scope of the invention is set out in the attached claims.

The invention claimed is:

1. A kit comprising an occlusion device, a pulse wave velocity (PWV) device and analysing means for analysing signals produced by the occlusion device and the PWV device, which devices and means are adapted to function cooperatively, wherein:
  - the occlusion device is for the non-invasive measurement of a subject's blood pressure and comprises:
    - area means for measuring the change in luminal area of an artery of the subject during a heartbeat;
    - contacting means for contacting a body part of the subject containing the artery and for having pressure exerted thereon, either by pressing the contacting means against the body part or by pressing the body part against the contacting means; and
    - pressure means for measuring the instantaneous pressure between the body part containing the artery and the contacting means;
  - the PWV device comprises:
    - measuring means for making measurements from which the PWV can be derived;
  - the analysing means is adapted to:
    - analyse the measured values of instantaneous pressure exerted on the contacting means and the change in luminal area so as to make a determination of the subject's blood pressure and, from the measurements made by the measuring means and the determined blood pressure, derive an improved estimate of blood pressure derived from PWV, wherein the kit is adapted to provide an estimate of systolic and diastolic blood pressure.

2. An integrated device comprising:
  - area means for measuring the change in luminal area of an artery of a subject during a heartbeat;
  - contacting means for contacting a body part of the subject containing the artery and for having pressure exerted thereon, either by pressing the contacting means against the body part or by pressing the body part against the contacting means;
  - pressure means for measuring the instantaneous pressure between the body part containing the artery and the contacting means;
  - measuring means for making measurements from which the pulse wave velocity (PWV) can be derived; and
  - analysing means which is adapted to analyse the measured values of instantaneous pressure exerted on the contacting means and the change in luminal area so as to make a determination of the subject's blood pressure and, from the measurements made by the measuring means and the determined blood pressure, derive an improved estimate of blood pressure derived from PWV.

3. The kit of claim 1, wherein the analysing means is further adapted to:

from measurements made by the measuring means, derive an estimate of the PWV;

from the estimate of the PWV, derive an estimate of the subject's blood pressure;

use the estimate of the subject's blood pressure derived from the estimate of the PWV to:

enhance the accuracy of the determined blood pressure;

speed up the processing of the measurements of instantaneous pressure and change in luminal area to make the determination of blood pressure; or improve the search strategy of optimisation techniques used by in making the determination of blood pressure.

4. The integrated device of claim 2, wherein the analysing means is further adapted to:

from measurements made by the measuring means, derive an estimate of the PWV;

from the estimate of the PWV, derive an estimate of the subject's blood pressure;

analyse the measured values of instantaneous pressure exerted on the contacting means and the change in luminal area so as to make a determination of the subject's blood pressure; and use the estimate of the subject's blood pressure derived from the estimate of the PWV to:

enhance the accuracy of the determined blood pressure;

speed up the processing of the measurements of instantaneous pressure and change in luminal area to make the determination of blood pressure; or improve the search strategy of optimisation techniques used by in making the determination of blood pressure.

5. The kit of claim 1, wherein the measuring means uses an electrical sensor to detect the electrical trigger of the heartbeat.

6. The kit of claim 1, which further includes means for instructing the user to adjust how hard the device is pressed against the body part or the body part pressed against the device.

7. The kit of claim 1, wherein the analysing means is adapted to make an estimate of arterial stiffness and to use that estimate to improve the accuracy of the estimate of blood pressure or the ease of analysing the PWV.

8. The kit of claim 1, wherein the analysing means is adapted to make an estimate of the stiffness of the tissue surrounding the artery and to use that estimate to improve the accuracy of the estimate of blood pressure or the ease of analysing the PWV.

9. The kit of claim 8, wherein the estimate of the stiffness of the tissue surrounding the artery includes an estimate of the state of hydration of the tissue.

10. The kit of claim 1, wherein the analysing means is adapted to estimate the Pre-Ejection Period.

11. The integrated device of claim 2, wherein the measuring means uses an electrical sensor to detect the electrical trigger of the heartbeat.

12. The integrated device of claim 2, which is adapted to provide an estimate of systolic and diastolic blood pressure.

13. The integrated device of claim 2, which further includes means for instructing the user to adjust how hard the device is pressed against the body part or the body part is pressed against the device.

14. The integrated device of claim 2, wherein the analysing means is adapted to make an estimate of arterial stiffness and to use that estimate to improve the accuracy of the estimate of blood pressure or the ease of analysing the PWV.

15. The integrated device of claim 2, wherein the analysing means is adapted to make an estimate of the stiffness of the tissue surrounding the artery and to use that estimate to improve the accuracy of the estimate of blood pressure or the ease of analysing the PWV.

16. The integrated device of claim 15, wherein the estimate of the stiffness of the tissue surrounding the artery includes an estimate of the state of hydration of the tissue.

17. The integrated device of claim 2, wherein the analysing means is adapted to estimate the Pre-Ejection Period.

* * * * *